(12) United States Patent
Sato

(10) Patent No.: US 8,182,403 B2
(45) Date of Patent: May 22, 2012

(54) PRESSURIZED-TRAINING APPARATUS AND CONTROL METHOD FOR THE SAME

(75) Inventor: Yoshiaki Sato, Tokyo (JP)

(73) Assignee: Sato Sports Plaza Co., Ltd., Tokyo (JP)

( * ) Notice: Subject to any disclaimer, the term of this patent is extended or adjusted under 35 U.S.C. 154(b) by 0 days.

(21) Appl. No.: 12/092,510

(22) PCT Filed: Nov. 2, 2006

(86) PCT No.: PCT/JP2006/322421
§ 371 (c)(1),
(2), (4) Date: Mar. 27, 2009

(87) PCT Pub. No.: WO2007/052844
PCT Pub. Date: May 10, 2007

(65) Prior Publication Data
US 2009/0221406 A1    Sep. 3, 2009

(30) Foreign Application Priority Data
Nov. 4, 2005 (JP) .................. 2005-321549

(51) Int. Cl.
*A63B 21/08* (2006.01)
(52) U.S. Cl. .......................... 482/113; 482/1
(58) Field of Classification Search ............... 482/8, 113
See application file for complete search history.

(56) References Cited

U.S. PATENT DOCUMENTS

| 5,791,348 | A | * | 8/1998 | Aung et al. ............... 600/493 |
| 6,283,922 | B1 | | 9/2001 | Goto et al. |

FOREIGN PATENT DOCUMENTS

| FR | 2 673 368 A | 9/1992 |
| JP | 07-144027 | 6/1995 |
| JP | 10-085361 | 4/1998 |
| JP | 10-085362 A | 4/1998 |
| JP | 2005-058544 A | 3/2005 |

OTHER PUBLICATIONS

European Search Report Dated Jan. 21, 2009.
International Search Report dated Jan. 30, 2007.

* cited by examiner

*Primary Examiner* — Loan Thanh
*Assistant Examiner* — Shila Jalalzadeh Abyane
(74) *Attorney, Agent, or Firm* — Edell, Shapiro & Finnan, LLC

(57) ABSTRACT

To improve the effect and the safety of Kaatsu training.
A training system includes a tight fitting device which is intended to be placed around a compressed range of an arm or a leg and which has a pneumatic bag, and a training device adapted to control the compression pressure that is applied to a compressed range by the tight fitting device by means of supplying air to the pneumatic bag of the tight fitting device or removing the air from the pneumatic bag. The training device supplies the air to the pneumatic bag and removes the air from the pneumatic bag in such a manner that the compression pressure that is applied by the tight fitting device to the compressed range oscillates between an upper peak and a lower peak within a range lower than an appropriate pressure.

12 Claims, 13 Drawing Sheets

PRESSURIZED-TRAINING APPARATUS AND CONTROL METHOD FOR THE SAME

TECHNICAL FIELD

The present invention relates to a training device for the muscle development. More particularly, the present invention relates to a training device suitable for Kaatsu training with which people having no motor abnormalities as well as people having motor abnormalities can develop their muscles in an effective manner.

BACKGROUND ART

The present inventor has conducted studies for some time in order to work out a muscle development method for easy, safe, and effective muscle development, and outcomes were compiled into a patent application having Japanese Patent Application No. 5-313949, which has been granted as Japanese Patent No. 2670421.

The muscle development method according to the patent in question is a distinctive and nonconventional one that involves the application of pressure. The muscle development method (hereinafter, referred to as the "Kaatsu Training™ method") is based on the following theoretical concept.

Muscles are composed of slow-twitch muscle fibers and fast-twitch muscle fibers. Slow-twitch muscle fibers are limited in their potential for growth. Accordingly, it is necessary to recruit fast-twitch muscle fibers of the slow- and fast-twitch muscle fibers in order to develop muscles. Recruitment of fast-twitch muscle fibers causes lactic acid buildup in the muscles, which triggers secretion of growth hormone from the pituitary. The growth hormone has effects of, for example, promoting muscle growth and shedding body fat. This means that recruitment and fatigue of fast-twitch muscle fibers results in development of fast-twitch muscle fibers and, in turn, the entire muscles.

Slow-twitch muscle fibers and fast-twitch muscle fibers are different from each other in terms of the following. Slow-twitch muscle fibers consume oxygen for energy and are recruited for low-intensity activities. On the other hand, fast-twitch muscle fibers provide for activities even when no oxygen is present. During high intense activities, the fast-twitch muscle fibers are recruited after the recruitment of the slow-twitch muscle fibers. This means that it is necessary to cause the earlier recruited slow-twitch muscle fibers to exhaust first in order to recruit fast-twitch muscle fibers.

Conventional muscle development method uses heavy exercises with, for example, a barbell to cause the slow-twitch muscle fibers to exhaust, and after which the fast-twitch muscle fibers are recruited. This approach requires a significant amount of exercises for the recruitment of the fast-twitch muscle fibers, is time-consuming, and tends to increase the burden on muscles and joints.

As an alternative approach, when doing muscle exercises with a predetermined range on the muscles near the proximal end of the limb being tightened by application of a pressure to restrict the blood flow to the distal portion from the tightened range, the slow-twitch muscle fibers which require oxygen for energy will be exhausted in a short period of time because of the reduced oxygen delivery to muscles. Thus, muscle exercises with blood-flow restriction by application of a pressure will result in recruitment of the fast-twitch muscle fibers without needing a large amount of exercises.

In addition, restriction of the blood flow by pressure application makes it hard to get the lactic acid that has built up in the muscles, out of the muscles. The lactic acid level is more likely to rise and a much larger amount of growth hormone is secreted, as compared with the case where the blood flow is unrestricted.

Based on this theoretical concept, restriction of the muscle blood flow can result in significant development of the muscles.

The Kaatsu training method is premised on the theoretical concept of muscle development by the restriction of the blood flow. More specifically, an appropriate compression pressure is applied to muscles at one or more predetermined range (s) near the proximal end of the limb to restrict the blood flow to the distal portion from the tightened range. The compression pressure puts on the muscles an appropriate load attributed to the decrease in blood flow, thereby causing muscle fatigue and, in turn, effective development of the muscles.

The Kaatsu training method has a remarkable feature of allowing muscle development without any exercises because of its mechanism of developing muscles by putting on the muscles a load attributed to the decrease in blood flow. With this feature, the Kaatsu training method is highly effective for the recovery of motor ability in people with impaired motor function, e.g., the elders or an injured person.

In addition, the Kaatsu training method can compensate for a total amount of load that is placed on the muscles by putting on the muscles a load attributed to reduced blood flow. When combined with some exercises, the method advantageously reduces an exercise-related load as compared with conventional methods. This feature produces effects of reducing possible risks of joint- or muscle-damages and shortening a necessary time period for training, because it can decrease the amount of muscle exercises for the muscle development.

It should be noted that, for the implementation of the Kaatsu training method, such a tool or device is essential that can restrict the blood flow through the muscles intended to be developed and that can precisely adjust the degree of blood flow restriction. In particular, the ability of precisely adjusting the degree of blood flow restriction in muscles is extremely important for a better effect as well as higher safety of the Kaatsu training method.

The present inventor has made studies for the Kaatsu training method and, in the course of these studies, devised an invention relating to a muscle development tool as disclosed in Japanese Patent Application No. 8-248317. The subject invention comprises a tight fitting device having a hollow band and a rubber-made pneumatic bag provided therein. Muscles are tightened and a desired compression pressure is applied thereto by introducing gas to the tube while the tight fitting device is placed around the muscles at a predetermined range.

Such type of a muscle development tool that uses gas for applying a pressure has an advantage of detailed control of the compression pressure by means of measuring the gas pressure within the pneumatic bag.

In addition, this type of a muscle development tool can vary the compression pressure to be applied to a compressed range of the limb merely by means of changing the gas pressure within the pneumatic bag. It is thus easy to vary the compression pressure with time.

The present inventor has performed the Kaatsu training using the muscle development tool of the type that uses gas to apply a pressure. During this process, the present inventor has noticed that the effects of the Kaatsu training can be improved when the compression pressure is controlled in a different manner from the one used conventionally.

Therefore, an object of the present invention is to provide a technique with which the effects of the Kaatsu training can be improved and the Kaatsu training can be expanded further.

SUMMARY OF THE INVENTION

As described above, the Kaatsu training involves application of a compression pressure to a predetermined range of the limb in order to restrict the blood flow to the distal portion from the tightened range of the limb, thereby to develop the muscles. The Kaatsu training can be used regardless of whether the limb receiving the compression pressure is exercised or is resting, but the muscles can be developed more effectively in combination with some exercises as described above.

The present inventor has noticed that, by increasing and decreasing a compression pressure for the Kaatsu training, a distal portion of the limb from the range receiving a compression pressure exhibited a similar phenomenon to that observed when the muscles of the same distal portion are exercised. This suggests that the limb receiving the compression pressure will have an effect similar to that obtained during intermittent exercises, merely by means of changing the compression pressure applied to a predetermined range of the limb.

The present inventor has made further studies according to this finding and has noticed the following two points.

First, the Kaatsu training for the same time period provides a higher effect when the Kaatsu training is performed while the compression pressure is increased and decreased than when the Kaatsu training is performed without any increase or decrease of the compression pressure, e.g., by means of continuously applying an appropriate constant compression pressure for the restriction of the blood to a predetermined range of the limb. This effect is hereinafter referred to as "training effect improvement effect".

The second notice is as follows.

There is a case where a normally-expected compression pressure should not be applied to a predetermined range of the limb during the Kaatsu training. This is because, when the person who receives the Kaatsu training is in poor physical condition or is not well familiar with the Kaatsu training, sudden application of a large compression pressure to the limb may cause stoppage of the blood flow rather than the restriction of it through the distal portion of the limb from the tightened range. The stoppage of the blood flow is potentially harmful to health of the person who receives the Kaatsu training, depending on its degree, instead of achieving an effect of the Kaatsu training. In such a case, the stoppage of the blood flow is less likely to be caused when a normally-expected compression pressure is applied after a compression pressure is varied up and down without exceeding the normally-expected compression pressure. Appropriate increase and decrease of the compression pressure can prevent almost completely the blood flow from being stopped. With this, effects of the Kaatsu training are achieved more easily and the safety of the kaatsu training is improved. This is the second point that the present inventor has noticed. This effect is hereinafter referred to as the "safety improvement effect".

In the present inventor's view, the reason why the safety improvement effect is obtained lies in the fact that the increase and decrease of the compression pressure within a pressure range below the normally-expected compression pressure would produce an effect of so-called warm-up exercises.

The present invention is based on the aforementioned findings of the present inventor that have obtained during the course of the repeated studies on the Kaatsu training. It is achieved by using a tight fitting device with which a compression pressure to be applied to a compressed range of the limb can be varied simply by means of changing the gas pressure within a pneumatic bag which facilitates increasing and decreasing of the compression pressure.

The invention based on the first point that the present inventor has noticed is as follows.

The invention is a training device used in combination with a tight fitting device comprising a band having a length sufficient to be placed around a predetermined range of a limb; an air-tight pneumatic bag provided in or on said band; and fastening means provided on said band, for fastening said band on the predetermined range when said band is placed around said predetermined range of the limb; the tight fitting device being adapted to apply a predetermined compression pressure to the predetermined range of the limb when said pneumatic bag is filled with gas, the predetermined compression pressure having a magnitude that causes restriction of the blood flow through a distal portion from the predetermined range, the training device being adapted to control said compression pressure. This training device comprises pressure adjusting means adapted to introduce gas into said pneumatic bag through a predetermined tube and to remove the gas from said pneumatic bag; and control means for controlling said pressure adjusting means to change said compression pressure. Said control means is adapted to control said pressure adjusting means in such a manner that said compression pressure that is applied by said tight fitting device to said predetermined range oscillates between levels of upper and lower peaks, the upper peak contained in an appropriate range of pressures to restrict the blood pressure through the distal portion from said predetermined range, the lower peak representing the level of a pressure lower than the next preceding upper peak.

The training device provides the aforementioned training effect improvement effect.

A equivalent effect to that obtained with this training device can be obtained through the following method.

The method is used in combination with a tight fitting device comprising a band having a length sufficient to be placed around a predetermined range of a limb; an air-tight pneumatic bag provided in or on said band; and fastening means provided on said band, for fastening said band on the predetermined range when said band is placed around said predetermined range of the limb; the tight fitting device being adapted to apply a predetermined compression pressure to the predetermined range of the limb when said pneumatic bag is filled with gas, the predetermined compression pressure having a magnitude that causes restriction of the blood flow through a distal portion from the predetermined range, the method being carried out by control means of a training device adapted to control said compression pressure, the training device comprising: pressure adjusting means adapted to introduce gas into said pneumatic bag through a predetermined tube and to remove the gas from said pneumatic bag; and said control means for controlling said pressure adjusting means to change said compression pressure. In this method, said control means controls said pressure adjusting means in such a manner that said compression pressure that is applied by said tight fitting device to said predetermined range continuously oscillates between levels of upper and lower peaks, the upper peak contained in an appropriate range of pressures to restrict the blood pressure through the distal portion from said predetermined range, the lower peak representing the level of a pressure lower than the next preceding upper peak.

The invention based on the second point that the present inventor has noticed is as follows.

The invention is a training device used in combination with a tight fitting device comprising a band having a length sufficient to be placed around a predetermined range of a limb; an air-tight pneumatic bag provided in or on said band; and fastening means provided on said band, for fastening said band on the predetermined range when said band is placed around said predetermined range of the limb; the tight fitting device being adapted to apply a predetermined compression pressure to the predetermined range of the limb when said pneumatic bag is filled with gas, the predetermined compression pressure having a magnitude that causes restriction of the blood flow through a distal portion from the predetermined range, the training device being adapted to control said compression pressure. The training device comprises pressure adjusting means adapted to introduce gas into said pneumatic bag through a predetermined tube and to remove the gas from said pneumatic bag; and control means for controlling said pressure adjusting means to change said compression pressure, said control means being adapted to control said pressure adjusting means in such a manner that said compression pressure that is applied by said tight fitting device to said predetermined range oscillates between levels of upper and lower peaks before it reaches to an appropriate pressure to restrict the blood pressure through the distal portion from said predetermined range, the upper peak contained in a range of pressures lower than the appropriate pressure, the lower peak representing the level of a pressure lower than the next preceding upper peak.

The training device provides the aforementioned safety improvement effect.

A equivalent effect to that obtained with this training device can be obtained through the following method.

The method is used in combination with a tight fitting device comprising a band having a length sufficient to be placed around a predetermined range of a limb; an airtight pneumatic bag provided in or on said band; and fastening means provided on said band, for fastening said band on the predetermined range when said band is placed around said predetermined range of the limb; the tight fitting device being adapted to apply a predetermined compression pressure to the predetermined range of the limb when said pneumatic bag is filled with gas, the predetermined compression pressure having a magnitude that causes restriction of the blood flow through a distal portion from the predetermined range, the method being carried out by control means of a training device adapted to control said compression pressure, the training device comprising: pressure adjusting means adapted to introduce gas into said pneumatic bag through a predetermined tube and to remove the gas from said pneumatic bag; and said control means for controlling said pressure adjusting means to change said compression pressure. In this method, said control means controls said pressure adjusting means in such a manner that said compression pressure that is applied by said tight fitting device to said predetermined range oscillates between levels of upper and lower peaks before it reaches to an appropriate pressure to restrict the blood pressure through the distal portion from said predetermined range, the upper peak contained in a range of pressures lower than the appropriate pressure, the lower peak representing the level of a pressure lower than the next preceding upper peak.

It is enough for the control means in the aforementioned invention having the safety improvement effect to control, as described above, the pressure adjusting means in such a manner that the compression pressure that is applied by the tight fitting device to the predetermined range of the limb oscillates between levels of upper and lower peaks before it reaches to an appropriate pressure to restrict the blood pressure through the distal portion from the predetermined range, the upper peak contained in a range of pressures lower than the appropriate pressure, the lower peak representing the level of a pressure lower than the next preceding upper peak.

For example, the control means may be adapted to control said pressure adjusting means in such a manner that the compression pressures that are applied by said tight fitting device to said predetermined range during said upper peaks on the second time and later are equal to or higher than the compression pressure applied by said tight fitting device to said predetermined range during the next preceding upper peak. In such a case, the compression pressure during the upper peak can be increased gradually because the compression pressure that is applied to the predetermined range of the limb during one upper peak is equal to or higher than the compression pressure during the next preceding upper peak. This can provide an effect similar to that obtained when intermittent exercises are performed at a gradually increasing intensity, so that there is a reduced risk of stoppage of the blood flow when an appropriate pressure to restrict the blood flow is applied to the limb. The control means may control the pressure adjusting means in such a manner that the level of the compression pressure that is applied by the tight fitting device to the predetermined range of the limb during the second or later upper peak(s) exceeds the level of the compression pressure that is applied by the tight fitting device to the predetermined range during the next preceding upper peak.

In addition, said control means may be adapted to control said pressure adjusting means in such a manner that said upper peaks and said lower peaks alternate with each other at least twice before said appropriate pressure is applied. The upper and the lower peaks repeated about this number of cycles can further reduce the risk of stoppage of the blood flow when an appropriate pressure to restrict the blood flow is applied to the limb. Of course, the upper and the lower peak may be repeated more number of times. About eight repeated cycles of the upper and the lower peaks can significantly reduce the risk of stoppage of the blood flow.

Said control means may also be adapted to control said pressure adjusting means in such a manner that it takes at least two minutes from the beginning of the first upper peak to the time instant at which said compression pressure reaches said appropriate pressure. This amount of time can further reduce the risk of stoppage of the blood flow when an appropriate pressure to restrict the blood flow is applied to the limb. Of course, a longer period of time may be used to alternate the upper and the lower peaks before an appropriate pressure to restrict the blood flow is applied to the limb.

The following applies to both the invention having the training effect improvement effect and the invention having the safety improvement effect.

Said control means may be adapted to control said pressure adjusting means in such a manner that said upper peak alternates with said lower peak in order to produce, even when the limb on which said tight fitting device is placed around is resting, the blood flow through the distal portion from said predetermined range that is similar to the blood flow obtained through the limb during intermittent exercises. By controlling the pressure adjusting means so that the upper and the lower peaks as described above are repeated, a better training effect improvement effect or a better safety improvement effect can be obtained.

Said control means may be adapted to control said pressure adjusting means in such a manner that the compression pressure that is applied by said tight fitting device to said predetermined range during said lower peak becomes lower by 30 mmHg than the compression pressure applied by said tight fitting device to said predetermined range during the next preceding upper peak. This indicates the relationship between the adjacent upper and lower peaks. With a difference of at least 30 mmHg between the levels of the compression pressure during the adjacent upper and lower peaks, the training effect improvement effect or the safety improvement effect can be obtained.

The compression pressures to be applied to the compressed range during the upper peak(s) and the lower peak(s) are determined appropriately depending on the sex, age, and a personal history of training of the person who receives the Kaatsu training as well as the type of the compressed range (i.e., whether the compressed range is on an arm or a leg). The compression pressures to be applied to the compressed range during the upper peak(s) and the lower peak(s) will have various values depending on the aforementioned conditions.

Said control means may be adapted to control said pressure adjusting means in such a manner that, when said predetermined range is on an arm, the compression pressure during said upper peak becomes approximately equal to the systolic blood pressure of the person who receives the Kaatsu training. This is the most general way of determining the compression pressure during the upper peaks. Accordingly, the systolic blood pressure of the person who receives the Kaatsu training would be one indication when determining the compression pressure during the upper peaks in the Kaatsu training for arms. Said control means may be adapted to control said pressure adjusting means in such a manner that, when said predetermined range is on a leg, the compression pressure during said upper peak becomes approximately equal to the systolic blood pressure plus 20 mmHg, of the person who receives the Kaatsu training. Accordingly, the systolic blood pressure plus 20 mmHg of the person who receives the Kaatsu training would be one indication when determining the compression pressure during the upper peaks in the Kaatsu training for legs.

Said control means may be adapted to control said pressure adjusting means in such a manner that the compression pressure during said lower peak becomes about 30 mmHg when the compression pressure during the next preceding upper peak is lower than 100 mmHg, and that the compression pressure during said lower peak becomes about 50 mmHg when the compression pressure during the next preceding upper peak is equal to or higher than 100 mmHg. This provides an indication in determining the values for the compression pressure that is applied by the tight fitting device to the compressed range of an arm or a leg during the lower peaks. The values are versatile common ones.

Said control means may be adapted to control said pressure adjusting means in such a manner that the compression pressure that is applied by said tight fitting device to said predetermined range during said lower peak becomes approximately equal to a natural compression pressure which is the compression pressure obtained when said tight fitting device is placed around said predetermined range. This means that the pressure within the pneumatic bag of the tight fitting device is adjusted to be around normal pressure during the lower peak.

The tight fitting device in the training device according to the present invention may be a single device or a combination of two or more devices. When two or more tight fitting devices are used, the pressure adjusting means may be equal in number to the tight fitting devices. The control means controls each of the pressure adjusting means equally or differently. When the number of the pressure adjusting means is two ore more and is equal to the number of the tight fitting devices, the number of the control means may be equal to the number of them.

A slight fluctuation of the compression pressure during a period of a single upper or lower peak can be tolerated when the upper or lower peak lasts for a certain period of time.

BEST MODES FOR CARRYING OUT THE INVENTION

Figure 1:
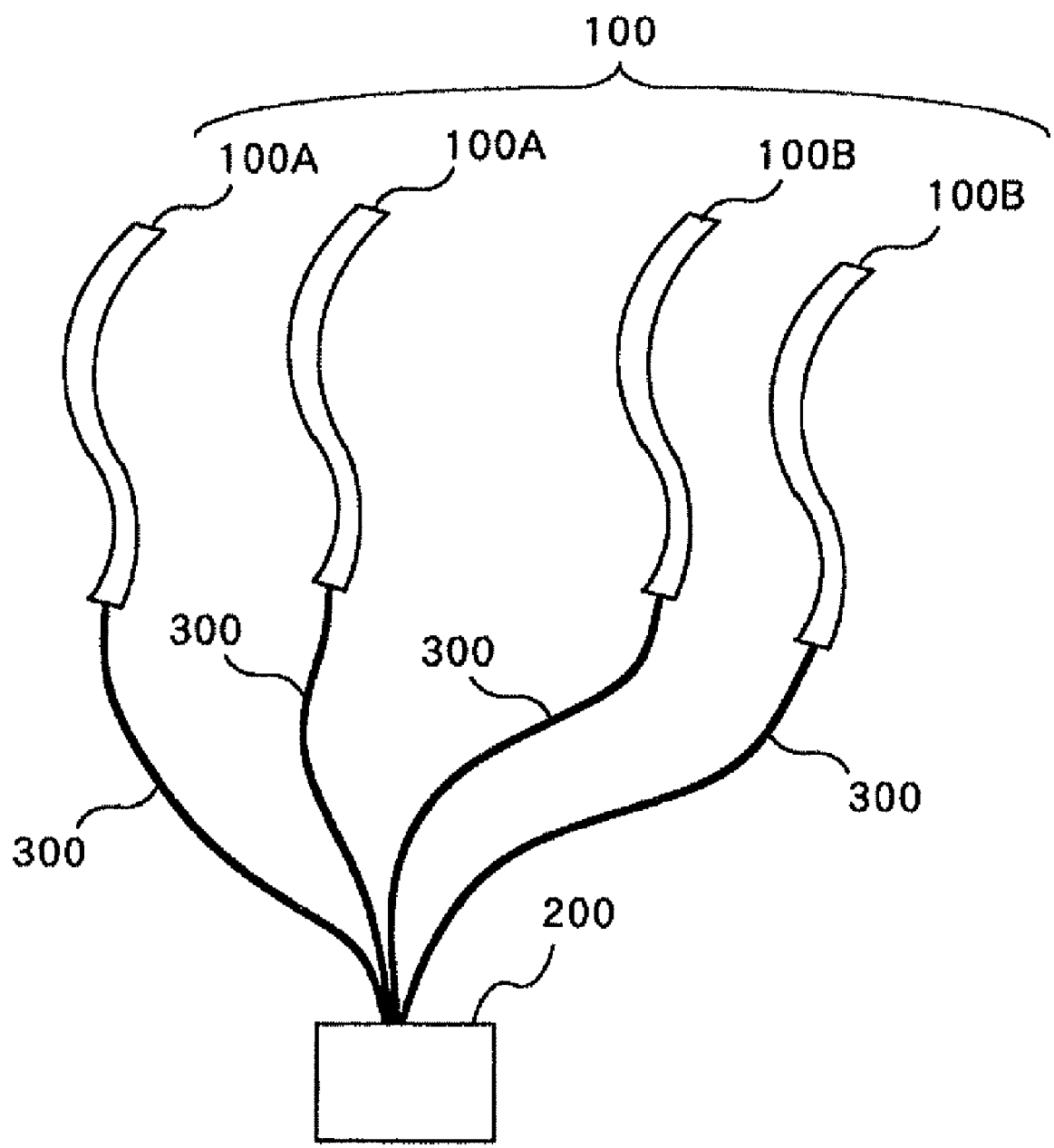
FIG. 1 is a view schematically showing the entire configuration of a training system according to an embodiment of the present invention.

Referring to the drawings, a preferred embodiment of the present invention is described.

FIG. 1 is a view schematically showing the entire configuration of a training system according to an embodiment of the present invention.

As shown in FIG. 1, the training system in this embodiment comprises a tight fitting device 100 and a training device 200.

Figure 2:
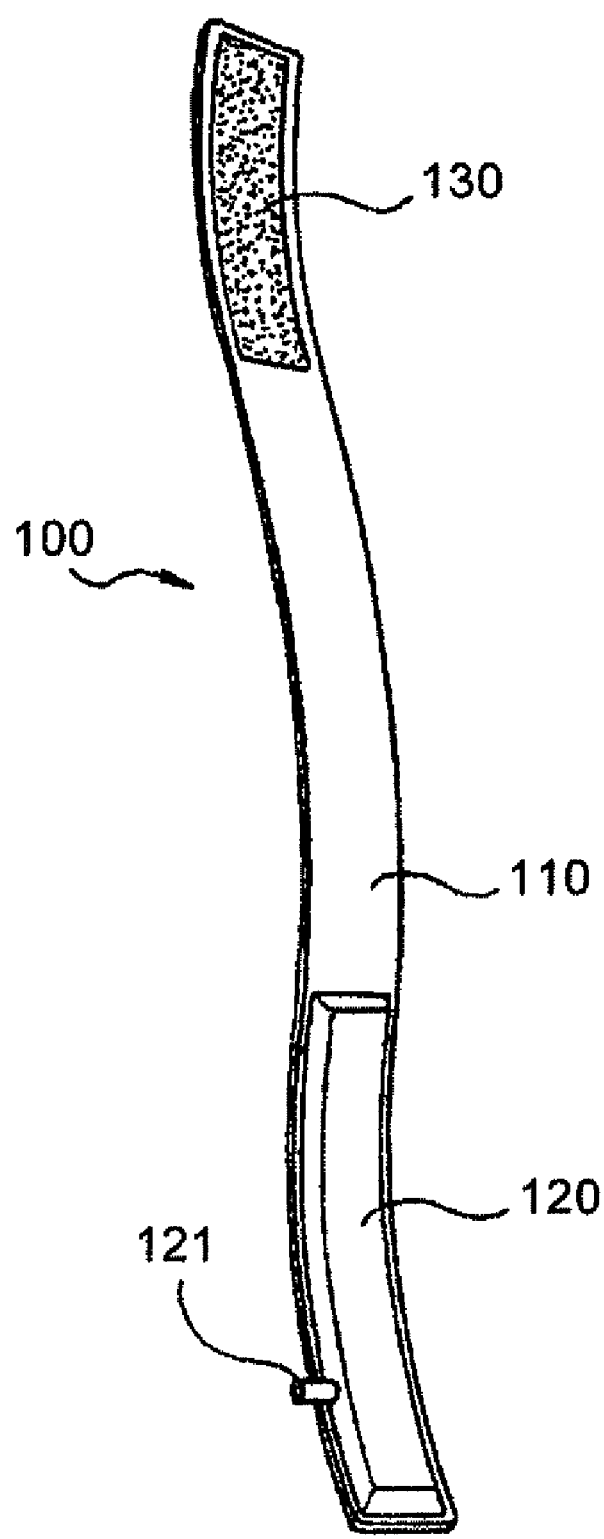
FIG. 2 is a perspective view showing a tight fitting device contained in the training system shown in FIG. 1.
Figure 3:
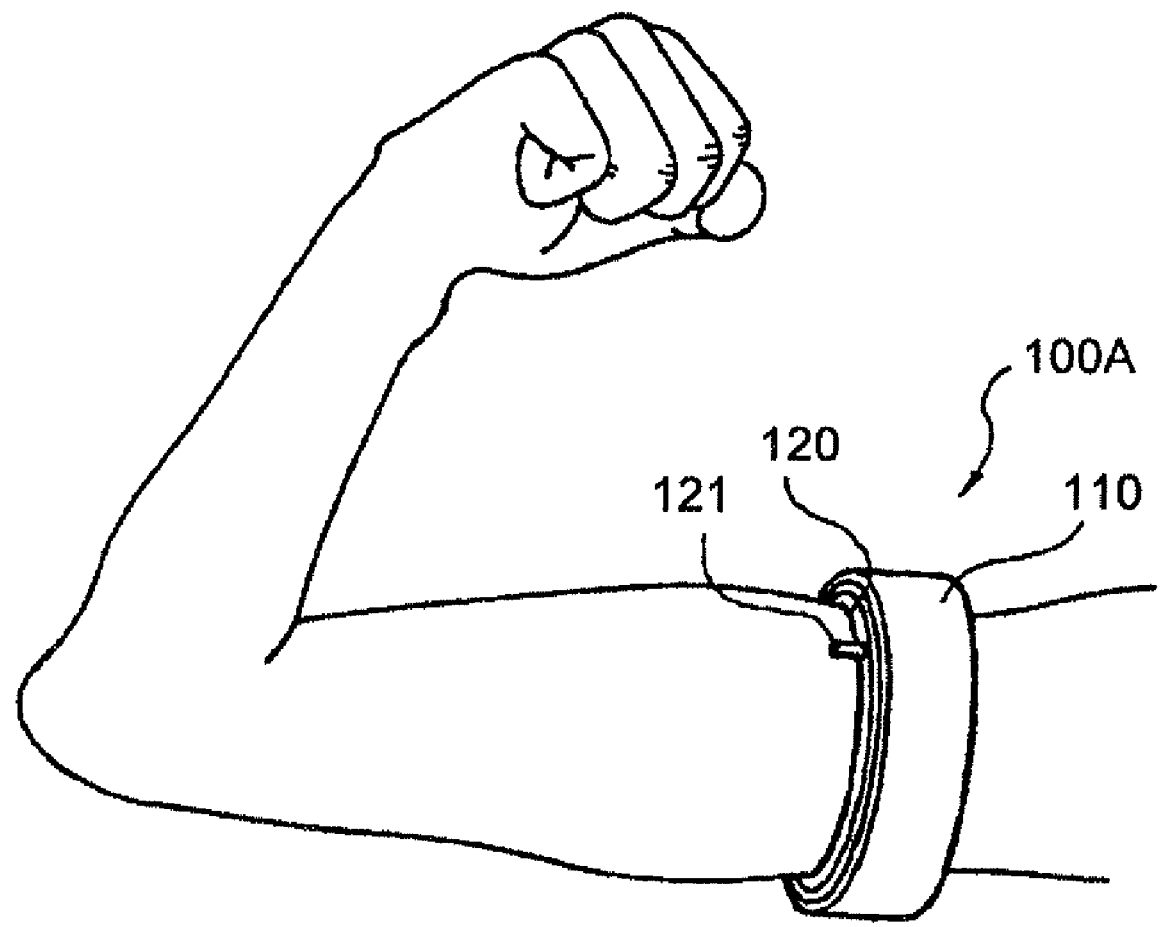
FIG. 3 is a view for use in describing how a tight fitting device for arms contained in the training system shown in FIG. 1 is used.
Figure 4:
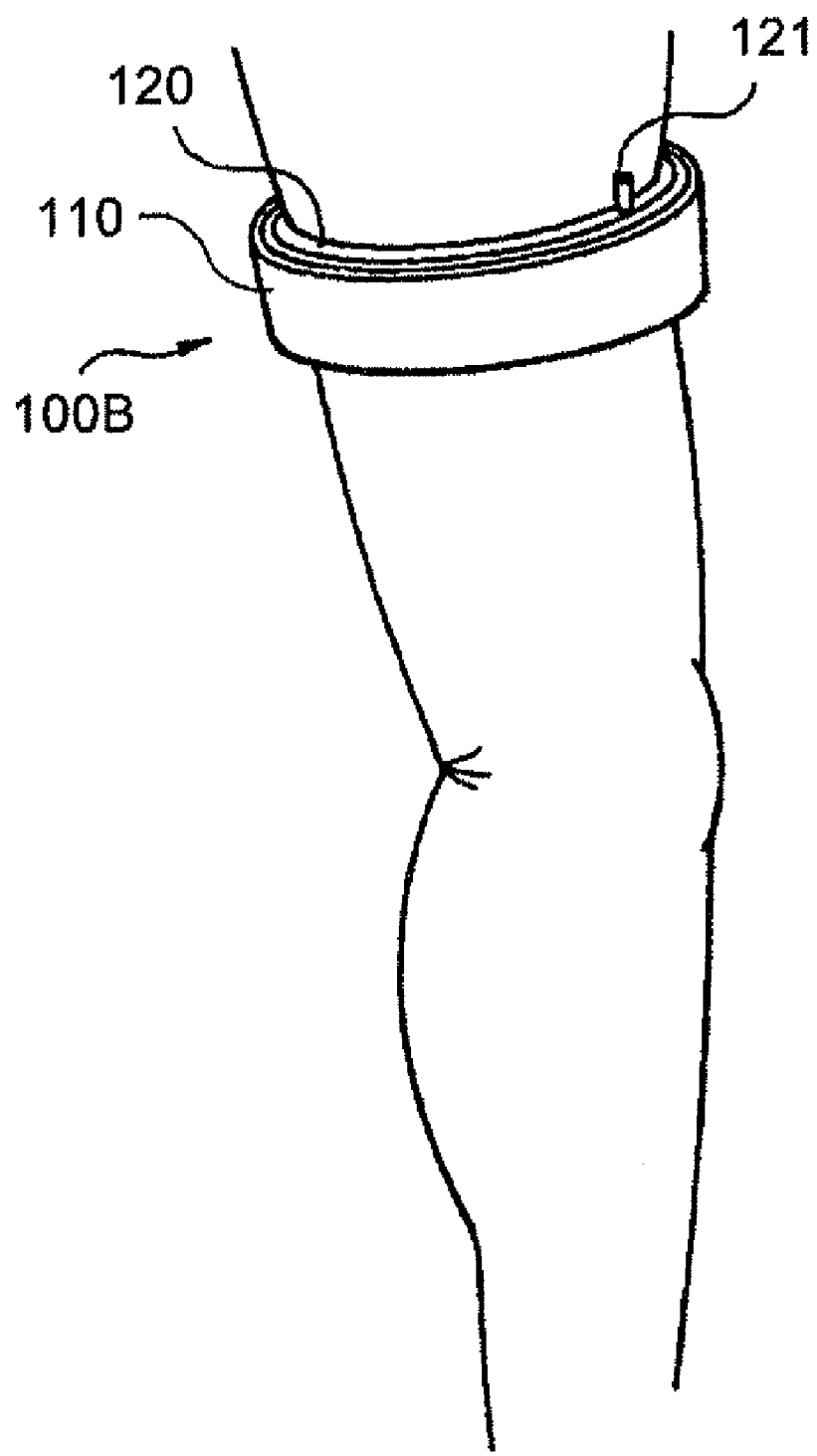
FIG. 4 is a view for use in describing how a tight fitting device for legs contained in the training system shown in FIG. 1 is used.

The tight fitting device 100 in this embodiment is configured in a manner as shown in FIGS. 2, 3, and 4. FIG. 2 is a perspective view showing an embodiment of the tight fitting device 100. FIGS. 3 and 4 are perspective views for use in describing how the tight fitting device 100 is used.

The tight fitting device 100 in this embodiment is a set of a plurality of, more specifically, four tight fitting devices as shown in FIG. 1. The reason why the number of the tight fitting devices 100 is four is to apply a pressure to both arms and legs of a person who uses the Kaatsu training method. Of the tight fitting devices 100 in this embodiment, tight fitting devices 100A are for arms (intended to be placed around each arm to apply a pressure thereto) whereas tight fitting devices 100B are for legs (intended to be placed around each leg to apply a pressure thereto). The number of the tight fitting devices 100 is not necessarily four. It may be any number equal to or larger than one. The number of the tight fitting devices 100A for arms is not necessarily the same as the number of the tight fitting devices 100B for legs. More than four tight fitting devices 100 may be used when two or more persons receive the Kaatsu training at once.

Each of the tight fitting devices 100 in this embodiment is intended to be placed around a predetermined range of muscles of any one of the limbs. It tightens the predetermined range of the muscles and applies a predetermined compression pressure to the predetermined range of the muscles. In addition, it can apply varying compression pressures to the predetermined range of an arm or a leg, as described below. Each of the tight fitting devices 100 basically comprises, in this embodiment, a band 110, a pneumatic bag 120 and a fastening member 130.

The band 110 may be any one of suitable materials as long as it can be placed around the predetermined range (the predetermined range is generally a position near the proximal end of an arm or the proximal end of a leg which the position is suitable for restricting the blood flow when tightened from outside; hereinafter, it is referred to as a "compressed range") where the tight fitting device 100 is placed around.

The band 110 in this embodiment is, but not necessarily so, made of an elastic or stretch material. More specifically, it is made of a neoprene rubber.

The band 110 in this embodiment may be determined depending on circumferential lengths of the compressed ranges (around which the tight fitting devices 100 are placed) of a person who uses the Kaatsu training method. The length of the band 110 is required to be longer than the circumferential lengths of the compressed ranges. The band 110 in this embodiment has a length more than the double of the circumferential lengths of the compressed ranges. The length of each band 110 for the tight fitting devices 100A for arms in this embodiment is determined in consideration with the circumferential length of 26 cm of an arm of the person who receives the Kaatsu training. Specifically, the length of the band is 90 cm. The length of each band 110 for the tight fitting devices 100B for legs is determined in consideration with the circumferential length of 45 cm of a leg of the person who receives the Kaatsu training. Specifically, the length of the band is 145 cm.

The width of the band 110 in this embodiment may suitably be determined for the compressed range around which the tight fitting device 100 is placed. For example, the band 110 for the tight fitting devices 100A for arms may have a width of about 3 cm, and the band 110 for the tight fitting devices 100B for legs may have a width of about 5 cm.

The pneumatic bag 120 is attached to the band 110. The pneumatic bag 120 in this embodiment is attached to the band 110 on one side thereof. The pneumatic bag 120 may be attached to the band 110 in a different manner. For example, the pneumatic bag 120 may be provided inside the band 110 when it is formed to have a hollow inner space.

The pneumatic bag 120 is, but not necessarily so, attached to the band 110 so that one end thereof is aligned to one end of the band 110 (the lower end of the band 110 in FIG. 2). The pneumatic bag 120 is an air-tight bag made of an air-tight material. The pneumatic bag 120 in this embodiment is made of, for example, an elastic or stretch rubber similar to that used for a rubber cuff in a machete. The material of the pneumatic bag 120 is not limited thereto. Any one of airtight material may be used.

The length of the pneumatic bag 120 in this embodiment is, but not necessarily so, approximately equal to the circumferential length of the compressed range. In this embodiment, each pneumatic bag 120 of the tight fitting devices 100A for arms has a length of 25 cm, and each pneumatic bag 120 of the tight fitting devices 110B for legs has a length of 44 cm.

The width of the pneumatic bag 120 may suitably be determined for the compressed range around which the tight fitting device 100 is placed. In this embodiment, the pneumatic bag 120 for the tight fitting devices 100A for arms has a width of about 3 cm, and the pneumatic bag 120 for the tight fitting devices 100B for legs has a width of about 5 cm, which does not always apply.

The pneumatic bag 120 has a connection port 121 communicated with the inside of the pneumatic bag 120. The connection port is used to connect to the training device 200 via a connection pipe 300 formed of a suitable tube such as a rubber tube. As will be described below, gas (air in this embodiment) is supplied to and removed from the pneumatic bag 120 via the connection port 121.

The fastening member 130 is for fastening the band 110 while it is placed around the compressed range. The fastening member 130 in this embodiment is a surface fastener provided on the same surface of the pneumatic bag 120 of the band 110 at the other end (the upper end of the band 110 in FIG. 2) of the band 110. The fastening member 130 can be fastened to any part of the entire surface of the band 110 on the side opposite to the pneumatic bag 120.

When air is supplied to the pneumatic bag 120 after the band 110 is placed around the compressed range and the band 110 is fastened by using the fastening member 130, the tight fitting device 100 compresses the muscles and applies the compression pressure. When the air is removed from the pneumatic bag 120 under such a circumstance, the compression pressure applied by the tight fitting device 100 to the muscles is reduced. A natural compression pressure in this invention represents the pressure that is applied by the tight fitting device 100 to the compressed range at the very beginning when the tight fitting device 100 is fastened.

The training device 200 is a device that can supply gas to the pneumatic bag 120 and can remove air from the pneumatic bag 120. In addition, the training device 200 performs automatic control of supplying and removing the gas to and from the pneumatic bag 120. The training device 200 may have any one of suitable configurations as long as it can supply gas to the pneumatic bag 120, can remove the gas from the pneumatic bag 120, and can perform the aforementioned automatic control.

Figure 5:
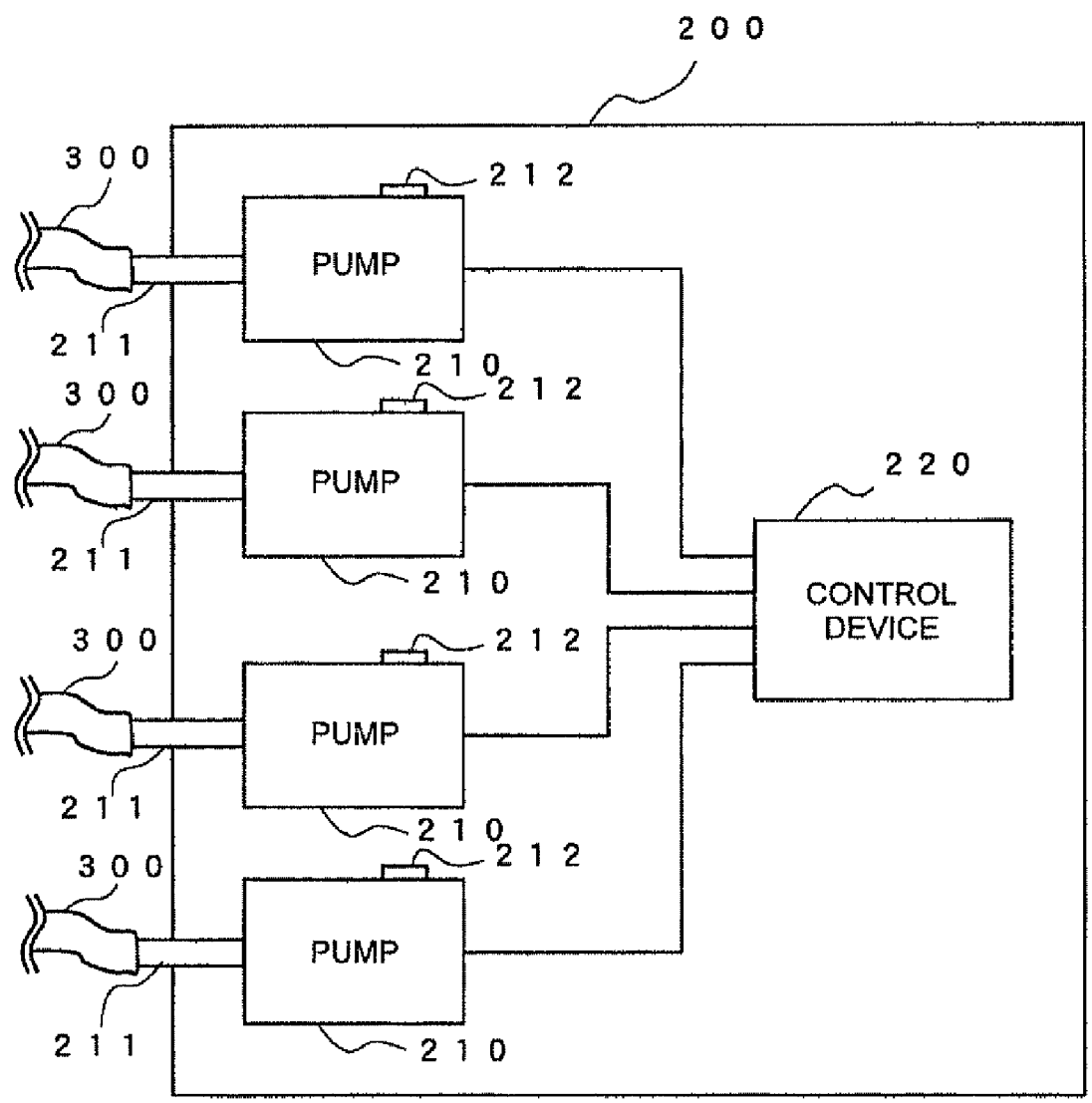
FIG. 5 is a view schematically showing an internal structure of a training device contained in the training system shown in FIG. 1.

A schematic illustration of an exemplary configuration of the training device 200 is given in FIG. 5. As shown in FIG. 5, the training device 200 comprises four pumps 210 and a control device 220. In this embodiment, the training device 200 has a casing in which the pumps 210 and the control device 220 are housed. An input device is provided outside the casing but it is not illustrated here.

The four pumps 210 are associated with four tight fitting devices 100, respectively. In this embodiment, the pumps 210 represent pressure adjusting means in the present invention.

Each of the pumps 210 has a function to suck the gas (air in this embodiment) that is present around it and supply the gas to the outside via a pump connection port 211 described below. The pump 210 has a valve 212 so that the gas within the pump 210 can be discharged to the outside by means of opening the valve 212. Each of the four pumps 210 has the pump connection port 211 and is connected to the pneumatic bag 120 through the connection pipe connected thereto and the connection port 121. When the pump 210 supplies the gas, the gas is introduced into the pneumatic bag 120. When the pump 210 opens the valve 212, the gas is removed from the pneumatic bag 120. The valve 212 is not necessarily provided on the pump 210. It may be provided at any position in the route from the pump 210 to the pneumatic bag 120.

The pump 210 contains a pressure gauge which is not shown with which the air pressure within the pump 210 can be measured. The air pressure within the pump 210 is, of course, equal to the air pressure within the pneumatic bag 120.

The control device 220 is for controlling the pump 210. The control device 220 controls the supply of air to the pneumatic bag 120 of the tight fitting device 100 by means of driving the pump 210 while the valve 212 is closed as well as the removal of the air within the pneumatic bag 120 while the valve 212 of the pump 210 is opened. That is, the control device 220 is for controlling the pump 210 including the opening and closing of the valve 212.

Figure 6:
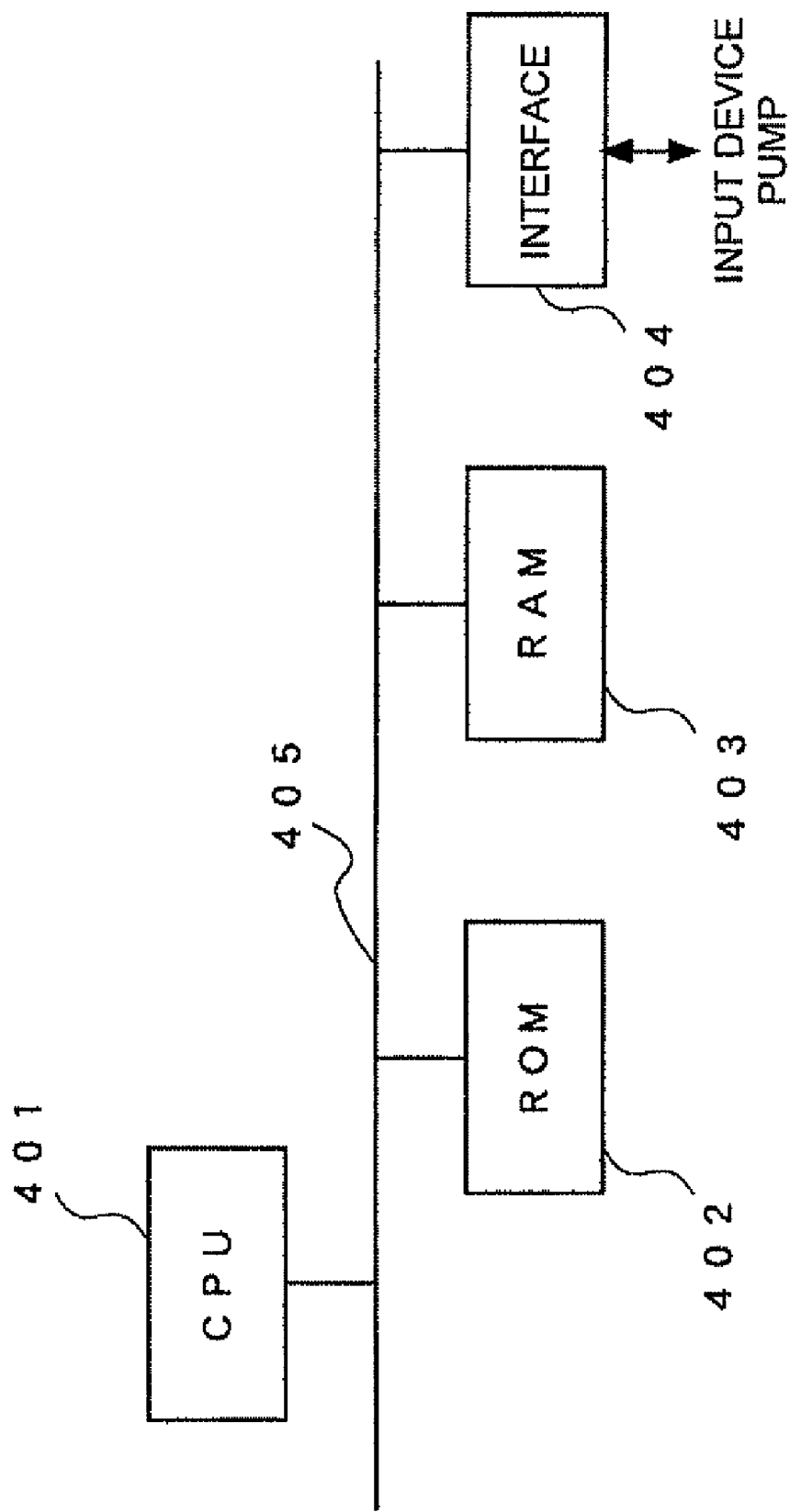
FIG. 6 is a view showing a hardware configuration of a control device contained in the system shown in FIG. 1.

An internal configuration of the control device 220 is shown in FIG. 6. The control device 220 comprises a computer therein. A CPU 401, a ROM 402, a RAM 403, and an interface 404 are connected to each other via a bus 405.

The CPU 401 is a central processing unit that controls the entire control device 220. The ROM 402 stores a program and data that are necessary for the processing described below, wherein the processing is carried out by the control device 220. The CPU 401 executes the processing according to the program. The ROM 402 may be embodied by using a flash ROM. In addition to the ROM 402 or along with the ROM 402, the control device 220 may comprise another recording medium such as a hard disk on which the aforementioned program and data are recorded. The RAM 403 is for providing a working area for the execution of the aforementioned program. The interface 404 has the functions to receive an input from an input device and to send a command issued by the control device 220 to each of the four pumps 210.

Figure 7:
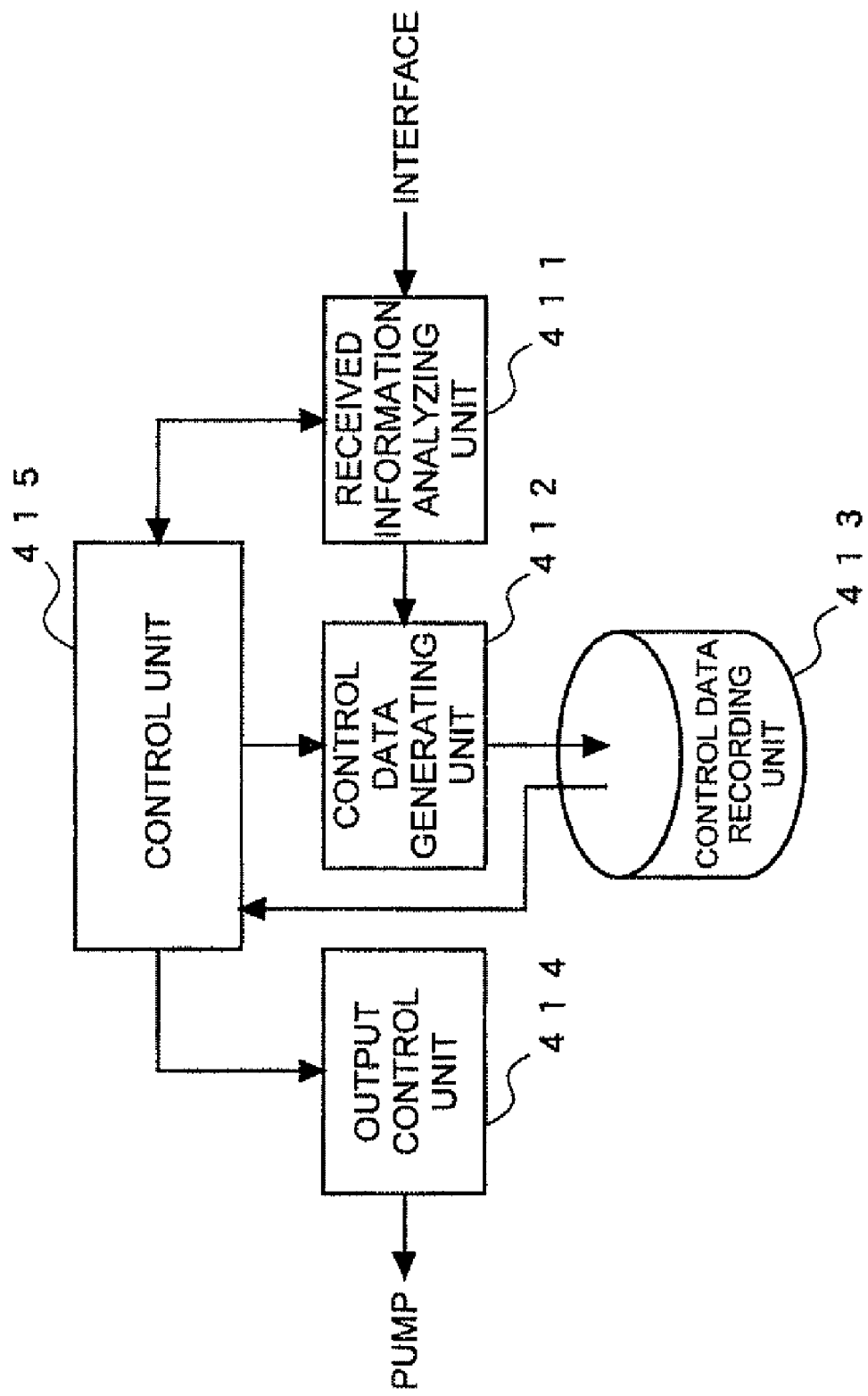
FIG. 7 is a view showing a functional block that is generated inside the control device contained in the system shown in FIG. 1.

As the CPU 401 executes the aforementioned program, a functional block as shown in FIG. 7 is created within the control device 220.

The control device 220 includes a received information analyzing unit 411, a control data generating unit 412, a control data recording unit 413, an output control unit 414, and a control unit 415.

The received information analyzing unit 411 receives an input from the input device via the interface 404 and analyzes the details thereof. Data representing the result of the analysis by the received information analyzing unit 411 is supplied to the control data generating unit 412 or to the control unit 415.

The control data generating unit 412 is for generating control data used to control the pump 210 including opening and closing of the valve 212, based on the data received from the received information analyzing unit 411. The control data generating unit 412 records the generated control data on the control data recording unit 413.

The control data recording unit 413 is for recording the control data supplied from the control data generating unit 412. The control data recording unit 413 in this embodiment records the control data associated with each of the four pumps 210 altogether as a set. The control data recording unit 413 in this embodiment is adapted to record two or more sets of control data about the four pumps 210. Each set of the data is the data for use in controlling application of a pressure to the arms and legs during the Kaatsu training. The two or more sets of the data are the data for two or more persons. In such a case, depending on who receives the Kaatsu training, the data for the person who receives the Kaatsu training are loaded. Alternatively, the two or more sets of data may be the data for a certain one person who receives the Kaatsu training. In such a case, one set of the different sets of the data may be loaded by the person according to his or her health conditions. Both the aforementioned two cases may be used in combination for the two or more sets of the data.

The control unit 415 is for controlling the received information analyzing unit 411, the control data generating unit 412, and the output control unit 414 as a whole. It has a function of controlling the modes described below. The control unit 415 also has functions of reading one set of the control data from the control data recording unit 413 and sending it to the output control unit 414, when the Kaatsu training is performed.

The output control unit 414 has a function of controlling the pump 210 in response to the control data. The Kaatsu training is performed while the output control unit 414 is operated to control the pump 210.

Next, how the Kaatsu training is performed using the training device 200 is described.

First, control data are generated.

The training device 200 according to the present invention is operated between two modes: a control mode and a training mode. The control data are generated in the control mode.

An input as to which one of the control mode and the training mode is selected is made with the input device. Upon reception of information from the input device as to which one of the control mode and the training mode is selected, the received information analyzing unit 411 that has received it via the interface 404 sends the information to the control unit 415. In response to this, the control unit 415 initiates either the control mode or the training mode.

In this training device 200, any information that is necessary for the generation of the control data can be supplied using the input device when the control mode is active. The supplied information is sent to the control data generating unit 412, via the interface 404 and the received information analyzing unit 411. The control data generating unit 412 generates the control data according to the information received thereby, and sends it to the control data recording unit 413. The control data recording unit 413 records the data. As described above, the control data in this embodiment are a set of four data each associated with the respective four pumps 210. The control data are the data indicating how the air pressure within the pump 210 is changed with time. How the air pressure within the pump 210 is changed with time will be described below.

In this embodiment, four control data are put together as a set, and two or more sets are recorded on the control data recording unit 413. Therefore, the aforementioned processing is repeated by the necessary number of times. As apparent from the above, in this embodiment, so-called "custom-made" control data are generated that are suited for the individual person who receives the Kaatsu training.

For the control data, typical or general control data may previously be recorded on the control data recording unit 413 before the shipment of the training device 200. The control data that are previously recorded on the control data recording unit 413 may be one or more.

After generation of the control data, the training device 200 is connected to the tight fitting device 100 through the connection pipe 300. Next, the tight fitting device 100 is placed around the compressed range as shown in FIGS. 3 and 4. The fastening member 130 is used to fasten it on the compressed range. Under such a circumstance, a natural compression pressure is applied to the compressed range. The compressed ranges in this embodiment are portions near the proximal ends of the arms and legs.

In this state, the training device 200 is switched to the training mode to initiate the Kaatsu training. The input device is operated in a suitable manner as described above in order to make the training device 200 operate in the training mode.

After the beginning of the training mode, the person who receives the Kaatsu training operates the input device to select his or her own set of four control data. If there are two or more sets of his or her own control data, an appropriate set of the control data is selected taking into consideration, for example, his or her health conditions. Selection of the control data is performed also by using the input device. Upon reception of the information as to which set of the control data is selected, from the input device, the information is supplied to the control unit 415 via the interface 404 and the received information analyzing unit 411. The control unit 415 reads the control data selected according to this information, out of the control data recording unit 413, and sends them to the output control unit 414. The output control unit 414 controls the pump 210 according to the control data. The pump 210 automatically keeps the air pressure within the pump 210 as indicated by the control data while measuring the air pressure within the pump 210 using a pressure gauge.

How the compression pressure to be applied to the compressed range is varied in this embodiment is described with reference to FIGS. 8 to 11.

The training device 200 described in this embodiment continuously carries out two modes in the training mode: a preparation mode and a normal mode. In this embodiment, the compression pressures (appropriate pressure) to be applied to arms and legs of the person who receives the Kaatsu training are 150 to 160 mmHg and 250 to 260 mmHg, respectively. The natural compression pressure is 50 mmHg for both arms and legs.

Figure 8:
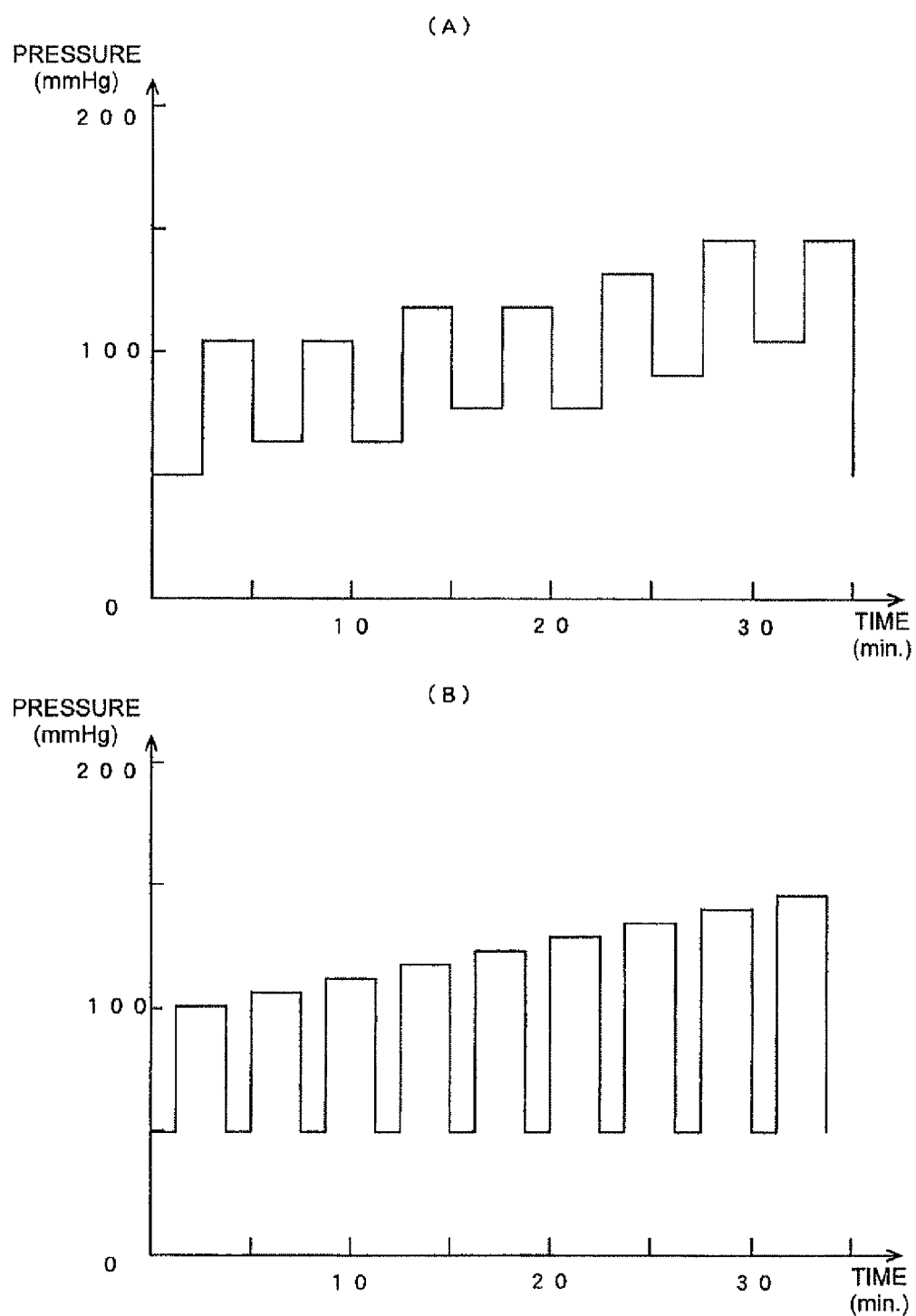
FIG. 8 is a view showing an exemplified variation over time of the compression pressure that is applied to a compressed range in a preparation mode for arms.
Figure 9:
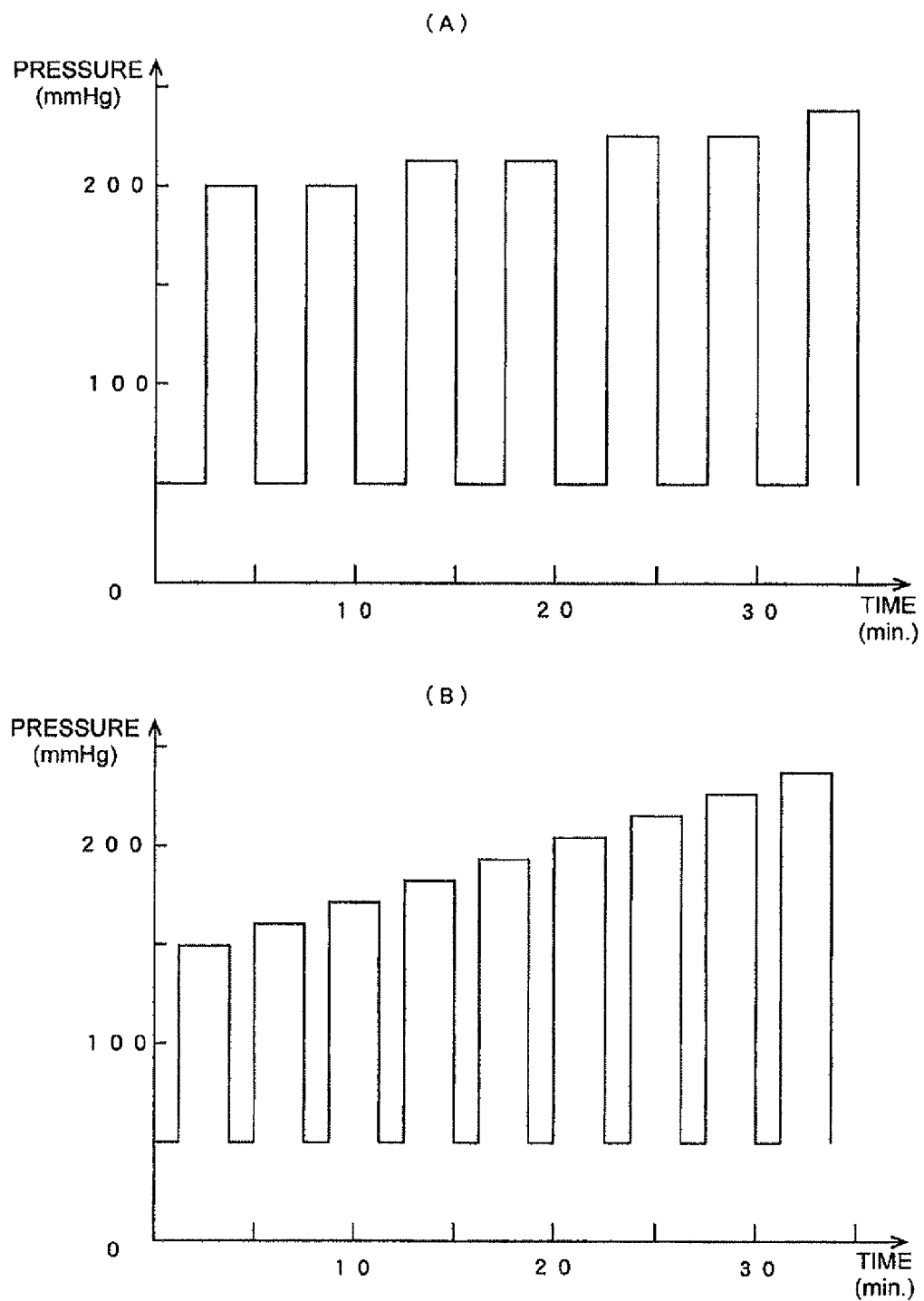
FIG. 9 is a view showing an exemplified variation over time of the compression pressure that is applied to a compressed range in a preparation mode for legs.

In the preparation mode, for example, the pumps 210 are controlled with the control data in such a manner that a pressure for compression as shown in FIGS. 8 and 9 is applied to an arm or a leg. Pressures in this embodiment are not applied to the arm(s) and the leg(s) at the same time. The pressure is, but not limited thereto, applied to the arm(s) first, and then to the leg(s) in this embodiment regardless of whether the operation is in the preparation mode or the normal mode.

In the preparation mode, the compression pressure is varied in such a manner that the compression pressure that is applied by the tight fitting device 100 to the compressed range oscillates between levels of upper and lower peaks, the upper peak contained in a range of pressures lower than an appropriate pressure, the lower peak representing the level of a pressure lower than the next preceding upper peak.

FIG. 8 shows a waveform of the compression pressure that is applied to the compressed range by the tight fitting device 100 in the preparation mode for arms.

In FIG. 3(A), the upper and the lower peaks alternate with each other at intervals of 2 minutes and 30 seconds. The time period during which the pressure is applied is equal to the time period during which no pressure is applied, in this embodiment. The preparation mode in this example is continued for 35 minutes. The number of repeat cycles of the upper and the lower peaks is, but not limited to, seven in this example. At the upper and the lower peaks in general, the identical compression pressures are repeated twice. It should be noted that, however, the fifth upper peak is not repeated at the same pressure. In this way, the upper and the lower peaks are not necessarily repeated regularly. In this example, each upper peak is determined to have a level equal to or higher than the next preceding upper peak. The same applies to the lower peaks. The compression pressure during the lower peak is determined to have a level lower by 37.5 mmHg than the next preceding upper peak. It should be noted that the lower peak is merely required to have a level lower by at least 30 mmHg than the next preceding upper peak. In practice, it takes several seconds for the compression pressure to be actually varied and thus the graph reflecting the change in compression pressure does not have vertical leading and trailing edges. However, in FIG. 8(A), the graph is intentionally drawn as a rectangular waveform for the purpose of simplicity. The same applies to the remaining graphs.

FIG. 8(B) shows an example where an upper peak having a period of about 2 minutes and 30 seconds alternates with a lower peak having a period of about 1 minute and 15 minutes. In this way, the time period during which the pressure is applied is not necessarily equal to the time period during which no pressure is applied. The preparation mode in this example is continued for just under 35 minutes. The number of repeat cycles of the upper and the lower peaks is nine in this example. The level of the upper peaks is increased stepwise, in which the level of each upper peak is increased by a constant amount from the level of the next preceding upper peak. In this example, the lower peaks are at the same level. In this example, each lower peak is kept at 50 mmHg which corresponds to the natural compression pressure. In this example, the valve 212 is fully opened at least during the initial time duration of the lower peak duration.

FIG. 9 shows a waveform of the compression pressure that is applied to the compressed range by the tight fitting device 100 in the preparation mode for legs.

In FIG. 9(A), the upper and the lower peaks alternate with each other at intervals of 2 minutes and 30 seconds. The time period during which the pressure is applied is equal to the time period during which no pressure is applied, in this embodiment. The preparation mode in this example is continued for 35 minutes. The number of repeat cycles of the upper and the lower peaks is seven in this example. At the upper and the lower peaks in general, the identical compression pressures are repeated twice. The last upper peak is not repeated at the same pressure. In this example, the upper peak is determined to have a level equal to or higher than the next preceding upper peak. The lower peaks all have a level which is equal to the natural compression pressure.

FIG. 9(B) shows an example where an upper peak having a period of about 2 minutes and 30 seconds alternates with a lower peak having a period of about 1 minute and 15 minutes. The preparation mode in this example is continued for just under 35 minutes. The number of repeat cycles of the upper and the lower peaks is nine in this example. The level of the upper peaks is increased stepwise, in which the level of each upper peak is increased by a constant amount from the level of the next preceding upper peak. In this example, the lower peaks are at the same level. In this example, each lower peak is kept at 50 mmHg which corresponds to the natural compression pressure.

The aforementioned preparation mode is followed by the normal mode.

In the normal mode, the compression pressure that is applied by the tight fitting device 100 to the compressed range oscillates between levels of upper and lower peaks, in which the upper peak represents a pressure within a range of appropriate pressures, and the lower peak represents the level of a pressure lower than the next preceding upper peak. In the normal mode, the upper and the lower peaks alternate with each other in such a manner that the blood flow through the distal portion from the compressed range becomes similar to that obtained through the limb during intermittent exercises of the limb, even when the limb around which the tight fitting device 100 is fastened is resting.

Figure 10:
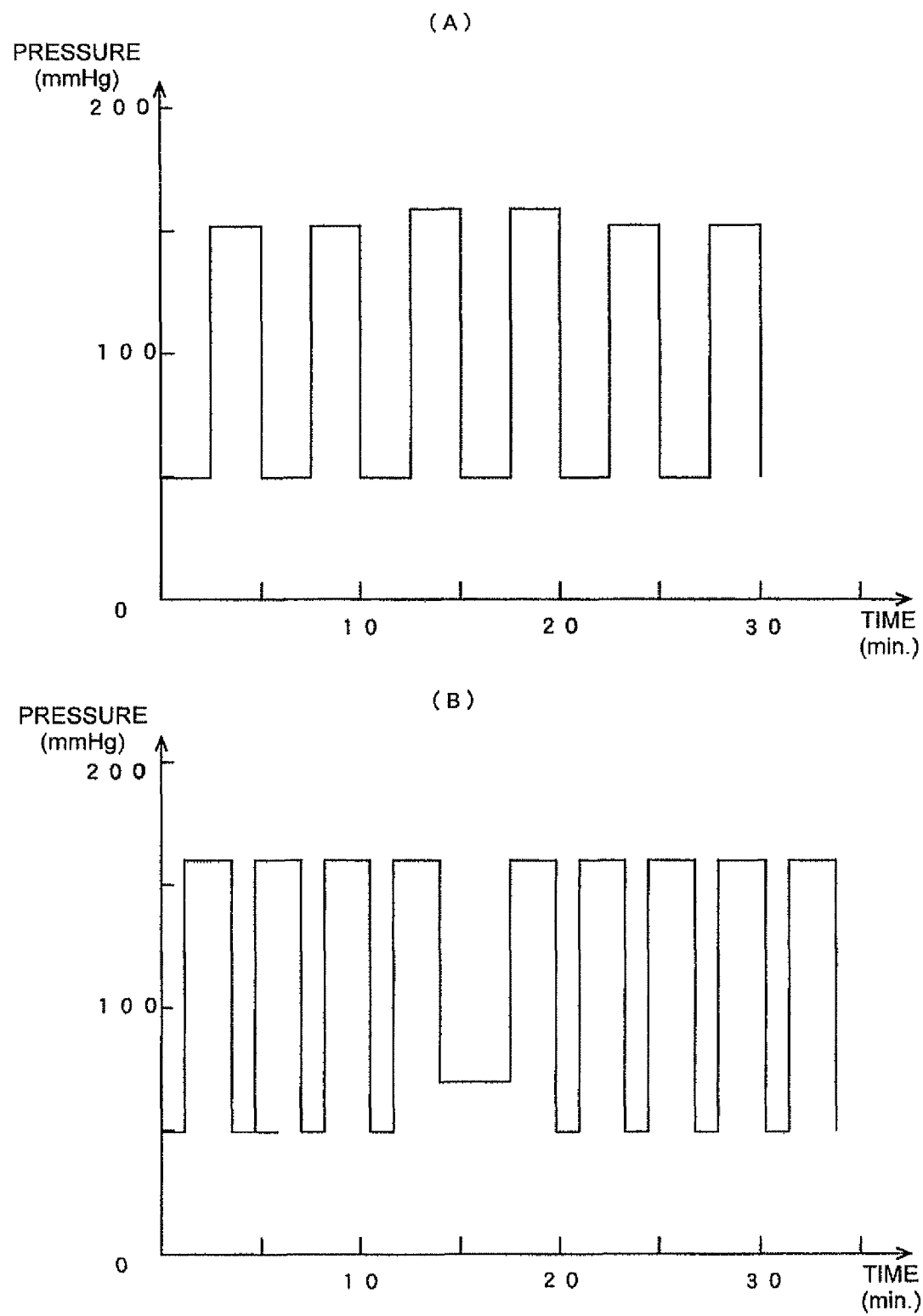
FIG. 10 is a view showing an exemplified variation over time of the compression pressure that is applied to a compressed range in a normal mode for arms.

FIG. 10 shows a waveform of the compression pressure that is applied to the compressed range by the tight fitting device 100 in the normal mode for arms.

FIG. 10(A) shows an example where the upper and the lower peaks alternate with each other at intervals of 2 minutes and 30 seconds. In this example, the time period during which the pressure is applied is equal to the time period during which no pressure is applied. The normal mode in this example is continued for 30 minutes. The number of repeat cycles of the upper and the lower peaks is, but not limited to, six in this example. For the upper peaks, the identical compression pressures are repeated twice. The upper peak may be varied or not as long as it falls within a range of appropriate pressures. The lower peak has a constant value of 50 mmHg which corresponds to the natural compression pressure. However, the lower peak is merely required to have a level lower by at least 30 mmHg than the next preceding upper peak.

FIG. 10(B) shows an example where an upper peak having a period of about 2 minutes and 30 seconds alternates with a lower peak having a period of about 1 minute and 15 minutes. As in the case of the preparation mode, the time period during which the pressure is applied is not necessarily equal to the time period during which no pressure is applied in the normal mode. In addition, this example has a longer lower peak than other lower peaks at about 15 minutes after the initiation of the normal mode. This longer lower peak serves as an interval for the Kaatsu training. In the normal mode as well as the preparation mode, the time periods of the upper peaks are not required to be equal to each other, and the time periods of the lower peaks are also not required to be equal to each other. The compression pressure that is applied during the aforementioned longer lower peak is slightly higher than the compression pressures applied during the other lower peaks, i.e., 50 mmHg. The compression pressures that are applied during the lower peaks are not required to be equal to each other. They are also not required to be identical with the natural compression pressure. The normal mode in this example is continued for just under 35 minutes. The number of repeat cycles of the upper and the lower peaks is nine in this example.

Figure 11:
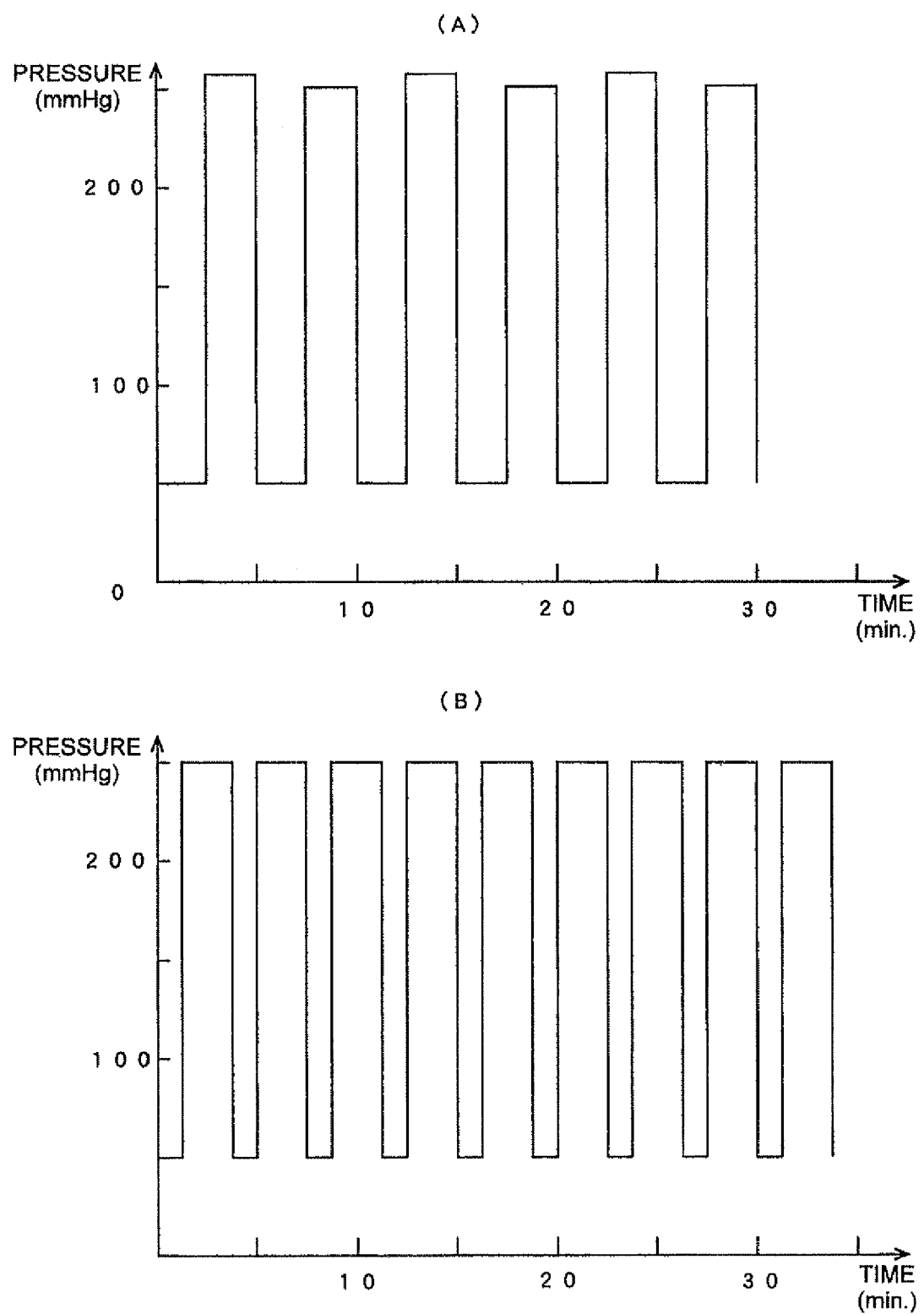
FIG. 11 is a view showing an exemplified variation over time of the compression pressure that is applied to a compressed range in a normal mode for legs.

FIG. 11 shows a waveform of the compression pressure that is applied to the compressed range by the tight fitting device 100 in the normal mode for legs.

FIG. 11(A) shows an example where the upper and the lower peaks alternate with each other at intervals of 2 minutes and 30 seconds. The time period during which the pressure is applied is equal to the time period during which no pressure is applied, in this embodiment. The normal mode in this example is continued for 30 minutes. The number of repeat cycles of the upper and the lower peaks is six in this example. The upper peaks are varied between 250 mmHg and 260 mmHg which are the appropriate pressures. The lower peak in this example has a constant value of 50 mmHg which corresponds to a natural pressure of compression.

FIG. 11(B) shows an example where an upper peak having a period of about 2 minutes and 30 seconds alternates with a lower peak having a period of about 1 minute and 15 minutes. The normal mode in this example is continued for just under 35 minutes. The number of repeat cycles of the upper and the lower peaks is nine in this example. The upper peaks in this example have a constant value of 250 mmHg. The lower peaks are also identical to each other in this example and are kept at 50 mmHg which corresponds to the natural compression pressure.

The compression pressures as described above are applied to the compressed range of the arm(s) or the leg(s) for the Kaatsu training. While the compression pressure is applied, the person who receives the Kaatsu training may either be resting or be doing exercises (light exercises would be enough). Even when the person who receives the Kaatsu training is resting, the blood flow through the distal portion from the compressed range of the arm(s) or the leg(s) becomes similar to that obtained through that range during exercises in the preparation mode, as in the normal mode.

<<Modified Version 1>>

A variation of the compression pressure that is applied to the compressed range in another example is described.

In this modified version, the training device 200 performs, in the training mode, two modes in sequence: the preparation mode and the normal mode. In this modified version, the pressure of 130 mmHg was used as the appropriate pressure for the arms of the person who receives the Kaatsu training, and the pressure obtained by adding 20 mmHg thereto, i.e., 150 mmHg was used as the appropriate pressure for the legs, taking into consideration that the person who receives the Kaatsu training had the systolic blood-pressure of 130 mmHg at that time, and that the person who receives the Kaatsu training has average health conditions and an average history of training and has limited experiences with the Kaatsu training.

The natural compression pressure was 50 mmHg for both the arms and the legs.

Figure 12:
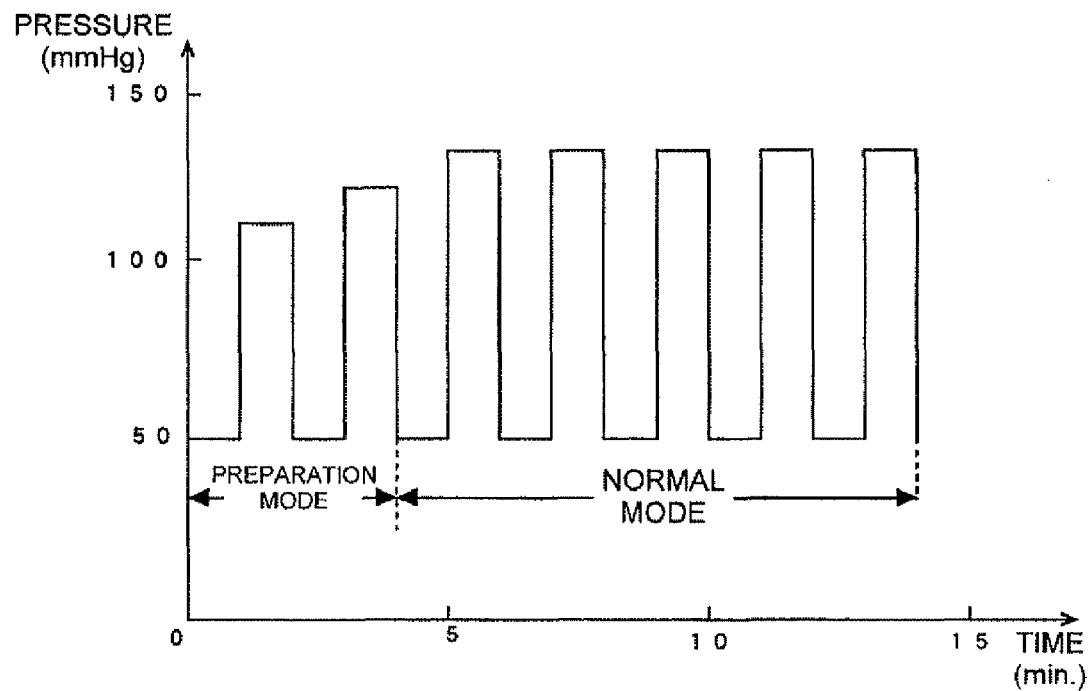
FIG. 12 is a view showing an exemplified variation over time of the compression pressure that is applied to a compressed range of an arm according to a modified version 1.

In the preparation mode for arms, as shown in FIG. 12, the upper peaks alternated with the lower peaks twice under the conditions that the compression pressures for the first and second upper peaks were 110 mmHg and 120 mmHg, respectively, and that the compression pressure for the lower peaks was 50 mmHg which corresponds to the natural compression pressure. The time period of each of the upper and the lower peaks is one minute.

Then, in the normal mode, the upper peaks alternated with the lower peaks five times under the conditions that the compression pressure for the upper peaks was 130 mmHg and that the compression pressure for the lower peaks was 50 mmHg.

Figure 13:
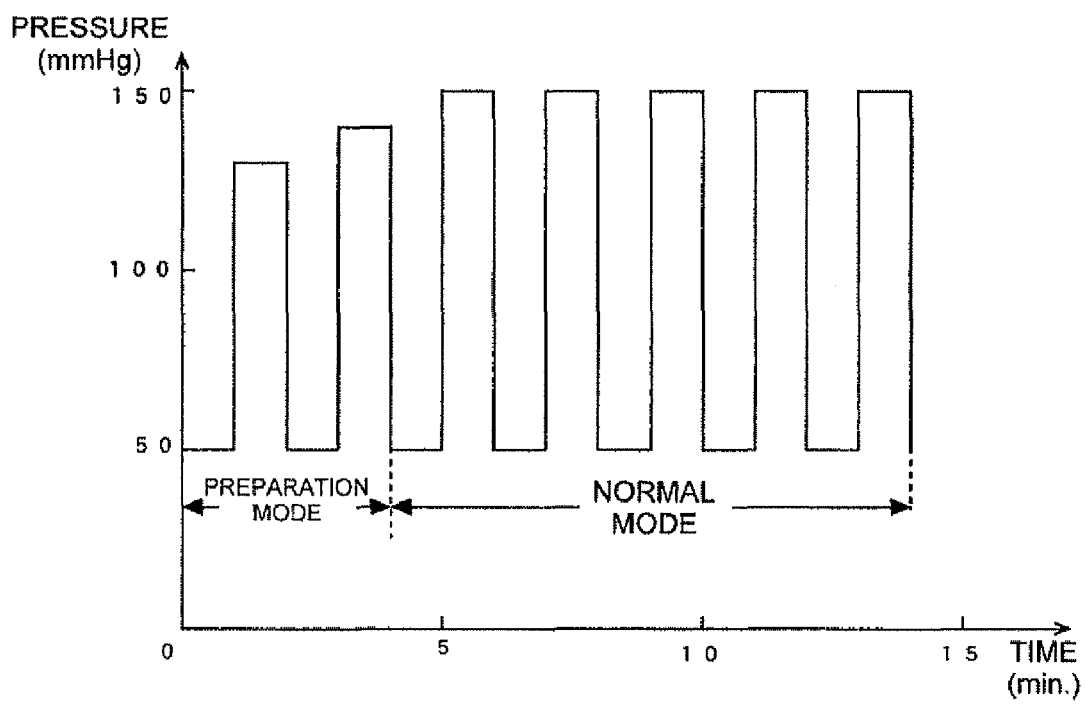
FIG. 13 is a view showing an exemplified variation over time of the compression pressure that is applied to a compressed range of a leg according to a modified version 1.

In the preparation mode for legs, as shown in FIG. 13, the upper peaks alternated with the lower peaks twice under the conditions that the compression pressure for the first upper peak was 130 mmHg, that the compression pressure for the second upper peak was 140 mmHg, and that the compression pressure for the lower peaks was 50 mmHg which corresponds to the natural compression pressure. The time period of each of the upper and the lower peaks is one minute.

Then, in the normal mode, the upper peaks alternated the lower peaks five times under the conditions that the compression pressure for the upper peaks was 150 mmHg and that the compression pressure for the lower peaks was 50 mmHg.

<<Modified Version 2>>

A variation of the compression pressure that is applied to the compressed range in another example is described.

In this modified version, the training device 200 performs, in the training mode, two modes in sequence: the preparation mode and the normal mode. In this embodiment, the pressures of 70 mmHg and 90 mmHg were used as the appropriate pressures for the arms and legs, respectively, of the person who receives the Kaatsu training, taking into consideration that the person who receives the Kaatsu training is elderly.

The natural compression pressure was 30 mmHg for both the arms and the legs.

Figure 14:
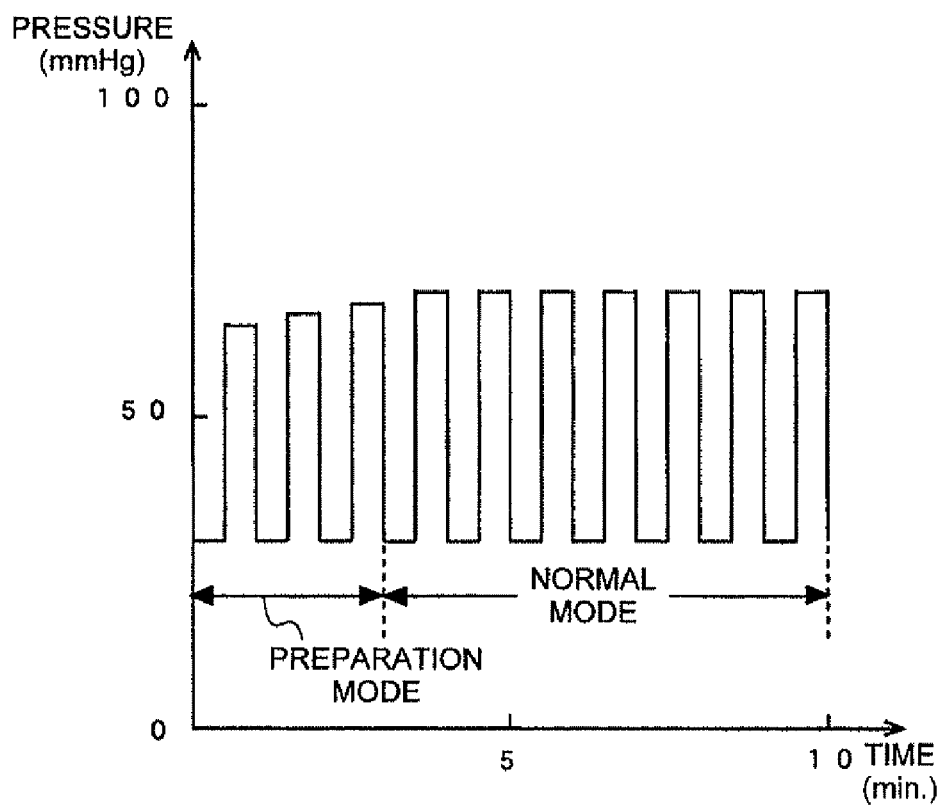
FIG. 14 is a view showing an exemplified variation over time of the compression pressure that is applied to a compressed range of an arm according to a modified version 2.

In the preparation mode for arms, as shown in FIG. 14, the upper peaks alternated the lower peaks three times under the conditions that the compression pressures for the first, second, and third upper peaks were 61 mmHg, 64 mmHg, and 67 mmHg, respectively, and that the compression pressure for the lower peaks was 30 mmHg which corresponds to the natural compression pressure. The time period of each of the upper and the lower peaks is 30 seconds.

Then, in the normal mode, the upper peaks alternated with the lower peaks seven times under the conditions that the compression pressure for the upper peaks was 70 mmHg and that the compression pressure for the lower peaks was 30 mmHg.

Figure 15:
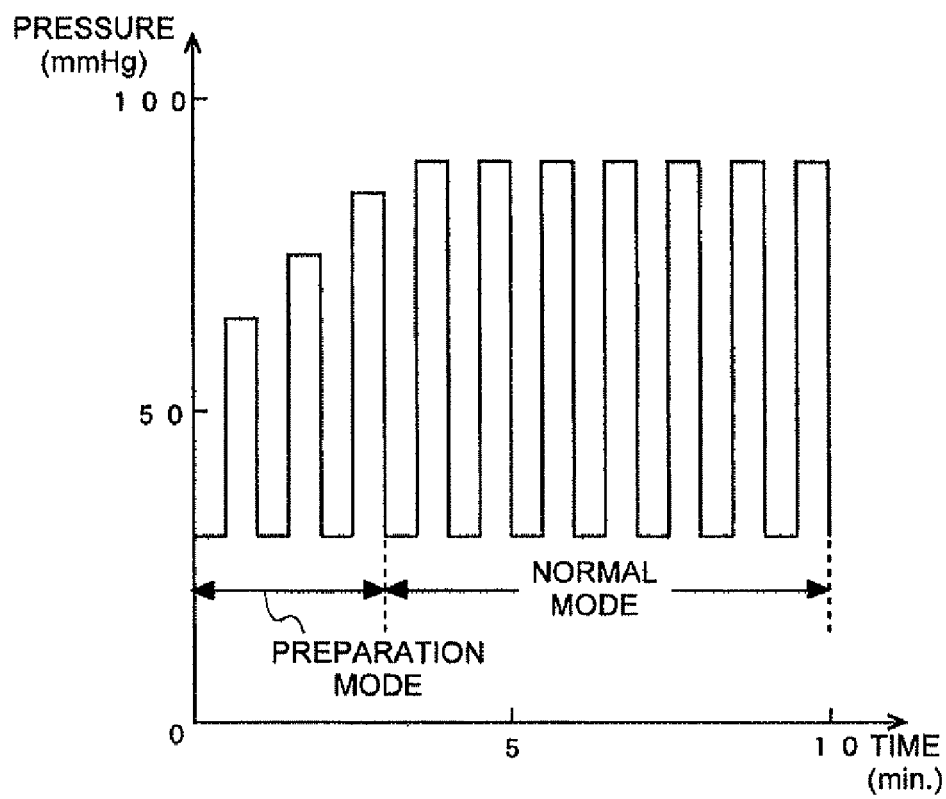
FIG. 15 is a view showing an exemplified variation over time of the compression pressure that is applied to a compressed range of a leg according to a modified version 2.

In the preparation mode for legs, as shown in FIG. 15, the upper peaks alternated with the lower peaks three times under the conditions that the compression pressures for the first, second, and third upper peaks were 65 mmHg, 75 mmHg, and 85 mmHg, respectively, and that the compression pressure for the lower peaks was 30 mmHg which corresponds to the natural compression pressure. The time period of each of the upper and the lower peaks is 30 seconds.

Then, in the normal mode, the upper peaks alternated with the lower peaks seven times under the conditions that the compression pressure for the upper peaks was 90 mmHg and that the compression pressure for the lower peaks was 30 mmHg.

The invention claimed is:

1. A training device used in combination with a tight fitting device comprising a band having a length sufficient to be placed around a predetermined part of a limb; an air-tight pneumatic bag provided in or on said band; and fastening means provided on said band, for fastening said band on the predetermined part of the limb when said band is placed around said predetermined part of the limb; the tight fitting device configured to apply a compression pressure to the predetermined part of the limb when said pneumatic bag is filled with gas, wherein the tight fitting device is further configured to apply a predetermined compression pressure having a magnitude that causes restriction of the blood flow to a distal portion of the limb, the training device configured to control said compression pressure, and comprising:

pressure adjusting means configured to introduce gas into said pneumatic bag through a predetermined tube and to remove the gas from said pneumatic bag; and control means for controlling said pressure adjusting means to change said compression pressure, said control means configured to read control data that indicate how the compression pressure is changed with time from recording means, and to control said pressure adjusting means, according to said control data, in such a manner that said compression pressure that is applied by said tight fitting device to said predetermined part of the limb oscillates between levels of upper and lower peaks, the upper peak contained in an appropriate range of pressures to restrict the blood pressure to a distal portion of the limb, the lower peak representing the level of a pressure lower than the next preceding upper peak, wherein said control means is adapted to control said pressure adjusting means in such a manner that the compression pressures that are applied by said tight fitting device to said predetermined part of the limb during said upper peaks on a second time and later times are equal to or higher than the compression pressure applied by said tight fitting device to said predetermined part of the limb during the next preceding upper peak, and wherein at least one of said upper peaks on the second time and later is equal to the compression pressure applied by said tight fitting device to said predetermined part of the limb during the next preceding upper peak.

2. The training device as claimed in claim 1, wherein said control means is adapted to control said pressure adjusting means in such a manner that said upper peak alternates with said lower peak in order to produce, even when the limb on which said tight fitting device is placed around is resting, the blood flow to a distal portion of the limb predetermined part that is similar to the blood flow obtained through the limb during intermittent exercises.

3. The training device as claimed in claim 1, wherein said control means is configured to control said pressure adjusting means in such a manner that the compression pressure that is applied by said tight fitting device to said predetermined part of the limb during said lower peak becomes lower by 30 mmHg than the compression pressure applied by said tight fitting device to said predetermined part of the limb during the next preceding upper peak.

4. The training device as claimed in claim 1, wherein said control means is configured to control said pressure adjusting means in such a manner that, when said predetermined part of the limb is on an arm of a person, the compression pressure during said upper peak becomes approximately equal to the systolic blood pressure of the person.

5. The training device as claimed in claim 1, wherein said control means is configured to control said pressure adjusting means in such a manner that, when said predetermined part of the limb is on a leg of a person, the compression pressure during said upper peak becomes approximately equal to the systolic blood pressure of the person plus 20 mmHg.

6. The training device as claimed in claim 1, wherein said control means is configured to control said pressure adjusting means in such a manner that the compression pressure during said lower peak becomes about 30 mmHg when the compression pressure during the next preceding upper peak is lower than 100 mmHg, and that the compression pressure during said lower peak becomes about 50 mmHg when the compression pressure during the next preceding upper peak is equal to or higher than 100 mmHg.

7. The training device as claimed in claim 1, wherein said control means is configured to adapted to control said pressure adjusting means in such a manner that the compression pressure that is applied by said tight fitting device to said predetermined part of the limb during said lower peak becomes approximately equal to a natural compression pressure which is the compression pressure obtained when said tight fitting device is placed around said predetermined part of the limb.

8. A training device used in combination with a tight fitting device comprising a band having a length sufficient to be placed around a predetermined part of a limb; an air-tight pneumatic bag provided in or on said band; and fastening means provided on said band, for fastening said band on the predetermined part of the limb when said band is placed around said predetermined part of the limb; the tight fitting device configured to apply a compression pressure to the predetermined part of the limb when said pneumatic bag is filled with gas, wherein the tight fitting device is further configured to apply a predetermined compression pressure having a magnitude that causes restriction of the blood flow to a distal portion of the limb, the training device configured to control said compression pressure, and comprising:

pressure adjusting means configured to introduce gas into said pneumatic bag through a predetermined tube and to remove the gas from said pneumatic bag; and control means for controlling said pressure adjusting means to change said compression pressure, said control means configured to read control data that indicate how the compression pressure is changed with time from recording means, and to control said pressure adjusting means, according to said control data, in such a manner that said compression pressure that is applied by said tight fitting device to said predetermined part of the limb oscillates between levels of upper and lower peaks before it reaches an appropriate pressure pressure to restrict the blood pressure to a distal portion of the limb, the upper peak contained in a range of pressures lower than the appropriate pressure, the lower peak representing the level of a pressure lower than the next preceding upper peak, wherein said control means is adapted to control said pressure adjusting means in such a manner that the compression pressures that are applied by said tight fitting device to said predetermined part of the limb during said upper peaks on a second time and later times are equal to or higher than the compression pressure applied by said tight fitting device to said predetermined part of the limb during the next preceding upper peak, and wherein at least one of said upper peaks on the second time and later is equal to the compression pressure applied by said tight fitting device to said predetermined part of the limb during the next preceding upper peak.

9. The training device as claimed in claim 8, wherein said control means is adapted to control said pressure adjusting means in such a manner that said upper peaks and said lower peaks alternate with each other at least twice before said appropriate pressure is applied.

10. The training device as claimed in claim 8, wherein said control means is adapted to control said pressure adjusting means in such a manner that it takes at least two minutes from the beginning of the first upper peak to the time instant at which said compression pressure reaches said appropriate pressure.

11. A control method used in combination with a tight fitting device comprising a band having a length sufficient to be placed around a predetermined part of a limb; an air-tight pneumatic bag provided in or on said band; and fastening means provided on said band, for fastening said band on the predetermined part of the limb when said band is placed around said predetermined part of the limb; the tight fitting device configured to apply a compression pressure to the predetermined part of the limb when said pneumatic bag is filled with gas, wherein the tight fitting device is further configured to apply a predetermined compression pressure having a magnitude that causes restriction of the blood flow to a distal portion of the limb, the method being carried out by control means of a training device configured to control said compression pressure, the training device comprising: pressure adjusting means configured to introduce gas into said pneumatic bag through a predetermined tube and to remove the gas from said pneumatic bag; and said control means for controlling said pressure adjusting means to change said compression pressure, said control means reads control data that indicate how the compression pressure is changed with time from recording means, and controls said pressure adjusting means, according to said control data, in such a manner that said compression pressure that is applied by said tight fitting device to said predetermined part of the limb continuously oscillates between levels of upper and lower peaks, the upper peak contained in an appropriate range of pressures to restrict the blood pressure to a distal portion of the limb, the lower peak representing the level of a pressure lower than the next preceding upper peak, wherein said control means controls said pressure adjusting means in such a manner that the compression pressures that are applied by said tight fitting device to said predetermined part of the limb during said upper peaks on a second time and later times are equal to or higher than the compression pressure applied by said tight fitting device to said predetermined part of the limb during the next preceding upper peak, and wherein at least one of said upper peaks on the second time and later is equal to the compression pressure applied by said tight fitting device to said predetermined part of the limb during the next preceding upper peak.

12. A control method used in combination with a tight fitting device comprising a band having a length sufficient to be placed around a predetermined part of a limb; an air-tight pneumatic bag provided in or on said band; and fastening means provided on said band, for fastening said band on the predetermined part of the limb when said band is placed around said predetermined part of the limb; the tight fitting device configured to apply a compression pressure to the predetermined part of the limb when said pneumatic bag is filled with gas, wherein the tight fitting device is further configured to apply a predetermined compression pressure having a magnitude that causes restriction of the blood flow to a distal portion of the limb, the method being carried out by control means of a training device configured to control said compression pressure, the training device comprising: pressure adjusting means configured to introduce gas into said pneumatic bag through a predetermined tube and to remove the gas from said pneumatic bag; and said control means for controlling said pressure adjusting means to change said compression pressure, said control means reads control data that indicate how the compression pressure is changed with time from recording means, and controls said pressure adjusting means, according to said control data, in such a manner that said compression pressure that is applied by said tight fitting device to said predetermined part of the limb oscillates between levels of upper and lower peaks before it reaches an appropriate pressure pressure to restrict the blood pressure to the distal portion of the limb, the upper peak contained in a range of pressures lower than the appropriate pressure, the lower peak representing the level of a pressure lower than the next preceding upper peak, wherein said control means controls said pressure adjusting means in such a manner that the compression pressures that are applied by said tight fitting device to said predetermined part of the limb during said upper peaks on a second time and later times are equal to or higher than the compression pressure applied by said tight fitting device to said predetermined part of the limb during the next preceding upper peak, and wherein at least one of said upper peaks on the second time and later is equal to the compression pressure applied by said tight fitting device to said predetermined part of the limb during the next preceding upper peak.

* * * * *